United States Patent
Baliga et al.

(10) Patent No.: US 10,006,071 B2
(45) Date of Patent: Jun. 26, 2018

(54) METHODS TO CONTROL SECRETION OF METABOLIC BYPRODUCTS IN ALGAE TO ENHANCE RECOVERY OF SAID BYPRODUCTS

(71) Applicant: Institute for Systems Biology, Seattle, WA (US)

(72) Inventors: Nitin S. Baliga, Seattle, WA (US); Monica V. Orellana, Seattle, WA (US); Kenia Whitehead, Seattle, WA (US); W. Lee Pang, Shoreline, WA (US)

(73) Assignee: Institute for System Biology, Seattle, WA (US)

( * ) Notice: Subject to any disclaimer, the term of this patent is extended or adjusted under 35 U.S.C. 154(b) by 516 days.

(21) Appl. No.: 14/572,550

(22) Filed: Dec. 16, 2014

(65) Prior Publication Data

US 2015/0132799 A1    May 14, 2015

Related U.S. Application Data

(62) Division of application No. 13/092,706, filed on Apr. 22, 2011, now Pat. No. 8,911,965.

(60) Provisional application No. 61/327,043, filed on Apr. 22, 2010, provisional application No. 61/389,142, filed on Oct. 1, 2010.

(51) Int. Cl.
| | |
|---|---|
| *C12N 1/12* | (2006.01) |
| *C12N 1/00* | (2006.01) |
| *C12N 1/04* | (2006.01) |
| *C12P 1/00* | (2006.01) |
| *C12P 39/00* | (2006.01) |
| *C12P 1/04* | (2006.01) |
| *C12P 7/14* | (2006.01) |
| *A01G 33/00* | (2006.01) |
| *C12Q 1/68* | (2018.01) |
| *G01N 33/68* | (2006.01) |

(52) U.S. Cl.
CPC .............. *C12P 39/00* (2013.01); *A01G 33/00* (2013.01); *Y02A 40/88* (2018.01)

(58) Field of Classification Search
CPC .... C12N 1/20; C12N 1/26; C12N 1/12; C12P 3/00; C12R 1/89; C07K 14/215
USPC ................. 435/257.1, 41, 42, 132, 134, 243
IPC ............. C07K 14/215; C12N 1/12,1/20; C12P 1/00
See application file for complete search history.

(56) References Cited

FOREIGN PATENT DOCUMENTS

| WO | WO-01/34092 | 5/2001 |
| WO | WO-2008/135382 | 11/2008 |

OTHER PUBLICATIONS

Skerman et al., 1980. Approved Lists of Bacterial Names. International Journal of Systematic Bacteriology, vol. 30, pp. 225-420.*
Perry et al 1997. Zinc Is a Potent Inhibitor of the Apoptotic Protease, Caspase-3. Journal of Biological Chemistry, vol. 272, pp. 18530-18533.*
Azam et al., "Microbial structuring of marine ecosystems," Nat. Rev. Micro. (2007) 5:782-791.
Azam, "Micorbial Control of Oceanic Carbon Flux: The Plot Thickens," Science (1998) 280:694-696.
Berges et al., "Physiological stress and cell death in marine phytoplankton: Induction of proteases in response to nitrogen or light limitation," Limnol. Oceanogr. (1998) 43:129-135.
Bidle et al., "Iron Starvation and Culture Age Activate Metacaspases and Programmed Cell Death in the Marine Diatom Thalassiosira pseudonana," Eukaryot. Cell (2008) 7:223-236.
Borisova et al., "Species composition of bacteria accompanying microalgae in culture (review of literature)," International Journal of Algae (2001) 2(4):115-126.
Giordano et al., "Gas Exchance and C Allocation in Dunaliella salina Cells in Response to the N Source and CO2 Concentration Used for Growth," Plant Physiology (1997) 115(3):1049-1056.
Giordano, "Interactions between C and N metabolism in Dunaliella salina cells cultured at elevated CO2 and high N concentrations," Journal of Plant Physiology (2001) 158(5):577-581.
International Search Report and Written Opinion for PCT/US2011/033637, dated Dec. 22, 2011, 16 pages.
Keshtacher et al., "Oligotrophic Bacteria Enhance Algal Growth under Iron-Deficient Conditions," Applied and Environmental Microbiology (1995) 61(6):2439-2441.
Lenova et al., "Development of Bacterial Microflora in Cultivation of Halophilous Algae of the Genus *Dunaliella*," Mikrobiologicezkij Zurnal (1984) 46(5):48-52.
Liska et al., "Enhanced Phtosynthesis and Redox Energy Production Contribute to Salinity Tolerance in Dunaliella as Revealed by Homology-Based Proteomics," Plant Physiol. (2004) 136:2806-2817.
Morris et al., "Relationship Between Light Carbon Dioxide Fixation and Dark Carbon Dioxide Fixation by Marine Algae," Limnology and Oceanography (1971) 16(6):854-858.
Oren, "Diversity of halophilic microorganisms: Environments, phylogeny, physiology, and applications," Journal of Industrial Microbiology & Biotechnology (2002) 28(1):56-63.
Oren et al., "Long-term mesocosm simulation of algal and archaeal blooms in the Dead Sea following dilution with Red Sea water," Natural Resources and Environmental Issues (2009) 15(Article 27):145-151.
Oren, "Microbial diversity and microbial abundance in salt-saturated brines: Why are the waters of hypersaline lakes red?" Natural Resources and Environmental Issues (2009) 15(Article 49):247-255.
Oren et al., "On the red coloration of saltern crystallizer ponds," Int. J. Salt Lake Res. (1992) 1(2):77-89.
Rahel et al., "Interrelationships between Dunaliella and halophilic prokaryotes in salern crystallizer ponds," Extremophiles: Life Under Extreme Conditions (2006) 12(1):5-14.

(Continued)

*Primary Examiner* — Louise Humphrey
*Assistant Examiner* — Kailash C Srivastava
(74) *Attorney, Agent, or Firm* — Morrison & Foerster LLP

(57) ABSTRACT

Methods are provided to control the harvesting of desired metabolic byproducts from hypersaline photosynthetic algae. Methods are presented to control secretion of said metabolic products in monocultures and co-cultures after accumulation of byproducts. The metabolic byproduct secretion is controlled by controlling caspase activity.

7 Claims, 2 Drawing Sheets

(56) References Cited

OTHER PUBLICATIONS

Segovia et al., "Inhibition of Caspase-Like Activities Prevents the Appearance of Reactive Oxygen Species and Dark-Induced Apoptosis in the Unicellular Chlorophyte Dunaliella Tertiolecta," Journal of Phycology (2009) 45(5):1116-1126.

Segovia et al., "Cell Death in the Unicellular Chlorophyte Dunaliella tertiolecta. A Hypothesis on the Evolution of Apoptosis in Higher Plants and Metazoans," Plant Physiol. (2003) 132:99-105.

* cited by examiner

METHODS TO CONTROL SECRETION OF METABOLIC BYPRODUCTS IN ALGAE TO ENHANCE RECOVERY OF SAID BYPRODUCTS

CROSS-REFERENCE TO RELATED APPLICATIONS

This application is a division of U.S. Ser. No. 13/092,706 filed 22 Apr. 2011, now U.S. Pat. No. 8,911,965 issued 16 Dec. 2014 which claims priority from U.S. Ser. No. 61/327,043 filed 22 Apr. 2010 and from U.S. Ser. No. 61/389,142 filed 1 Oct. 2010. The contents of these documents are incorporated herein by reference.

ACKNOWLEDGEMENT OF GOVERNMENT SUPPORT

This invention was made in part with grant support from the U.S. Government. The U.S. Government has certain rights in this invention.

TECHNICAL FIELD

The invention relates in part to improved methods to enhance carbon fixation in photosynthetic algae. More particularly, it relates to co-culturing algae with heterotrophic bacteria and archaea. In addition, it is directed to methods to control secretion by photosynthetic algae of desired metabolites or other dissolved organic molecules by specific control of apoptosis.

BACKGROUND ART

The use of photosynthetic algae to produce biofuels is an active area of research and development. Many projects are underway to improve the capability of photosynthetic algae to manufacture metabolites that are useful as sources of energy. In order to provide metabolites useful as biofuels, the algae must be encouraged to fix inorganic carbon into organic molecules, especially dissolved organic metabolites, that can be directed by the metabolic pathways of the algae into compounds useful as biofuels. Manipulation of the metabolic pathways of algae to divert the dissolved organic metabolites into compounds useful as biofuels may be achieved by standard genetic engineering techniques.

Further, in nature, microbial processes are coupled whereby photosynthetic primary producers of fixed carbon release carbon and nitrogen based dissolved organic matter that is assimilated and remineralized by heterotrophic bacteria and archaea. Azam, F., et al., *Nat. Rev. Micro.* (2007) 5:966, Azam, F., *Science* (1998) 280:694-696. In some case, biopolymers are released by virtue of apoptosis of the photosynthetic organism. Berges, J. A., et al., *Limnol. Oceanogr.* (1998) 43:129-135, Bidle, K. D., et al., *Eukaryot. Cell* (2008) 7:223-236.

The photosynthetic alga *Dunaliella salina* (*D. salina*) is the primary photosynthetic organism operative in halophilic environments wherein in such environments *D. salina* employ $CO_2$ assimilation to produce and store glycerol for use as an osmoprotectant at intracellular concentrations as high as 7M. Liska, A. J., et al., *Plant Physiol.* (2004) 136:2806-2817. It has also been shown that when exposed to darkness, this alga releases metabolites due to apoptosis as the release can be blocked by caspase inhibitors. Segovia, M., et al., *Plant Physiol.* (2003) 132:99-105.

DISCLOSURE OF THE INVENTION

The invention provides an improved method to culture hypersaline photosynthetic algae such as *Dunaliella salina* to achieve enhanced levels of fixed carbon at least two-fold or higher above those obtained previously. Thus, inorganic carbon is converted into small organic compounds and/or structural organic compounds which are useful in a variety of applications.

In addition, the invention provides a mechanism to control release of desired metabolites or organic matter in general by such photosynthetic algae by providing caspase inhibitors to prevent premature apoptosis and then removing the influence of the inhibitor to release the desired compounds at the appropriate time. This measure of control may be practiced on monocultures of the algae as well as co-cultures as described herein.

Thus, in one aspect, the invention is directed to a method to enhance fixation of inorganic carbon in a culture of hypersaline photosynthetic algae which method comprises co-culturing said algae with cells of other species, including but not limited to halophilic archaea (hereon "haloarchaea"). The co-culture may be subjected to cycles of illumination and darkness. Secretion of the product may result. The cycles of light and darkness, in one embodiment, mimic the diurnal cycle.

In another aspect, the invention is directed to co-cultures of hypersaline photosynthetic algae with heterotrophic bacteria or archaea, in particular with haloarchaea.

In one embodiment, the culture of hypersaline photosynthetic algae is co-cultured with heterotrophic bacteria or archaea, in particular with haloarchaea and also subjected to cyclic illumination and darkness.

In still another embodiment, the invention is directed to a method to control release of metabolites containing fixed carbon from hypersaline photosynthetic algae by periodic treatment with caspase inhibitors and time-structured removal thereof.

MODES OF CARRYING OUT THE INVENTION

Figure 1:
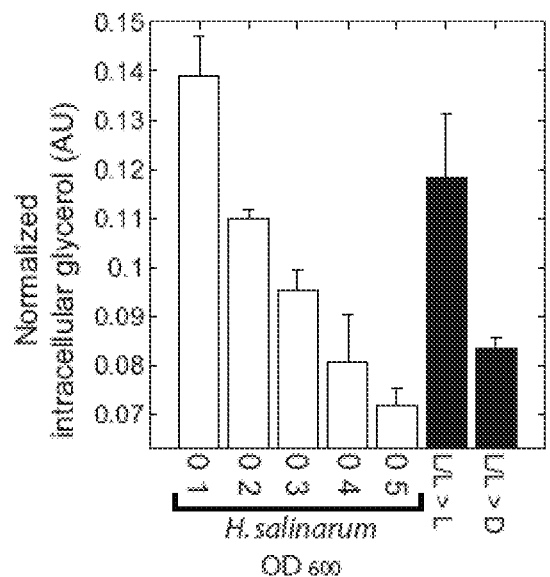
FIG. 1 is a graph showing the effect of the density of *Halobacterium salinarum* (*H. salinarum*) in co-culture with *D. salina* on intracellular glycerol in *D. salina*.

The invention provides an improved method to produce desired carbon-based biological material from photosynthetic algae on a continuous basis optionally with secretion of the desired product. Such products include biofuels, including lipids and long chain alkanes, as well as small molecule metabolites and drug precursors. The products may also be used as nutritional supplements. The time of secretion of the desired products may also be controlled by the method of the invention by controlling the presence and absence of caspase inhibitors.

The increased carbon fixation by the photosynthetic algae according to the method of the invention provides a method to enhance the utility of these organisms for a variety of purposes. As is well known in the art, these organisms are sources of nutritional supplements, pharmacologically important compounds, and materials that can be used as biofuels per se. The compounds into which the fixed carbon is initially included may be themselves harvested, or by suitable manipulation of the metabolic and anabolic pathways of such organisms using known genetic engineering techniques, they may be converted to alternative molecules that are of greater interest. In addition, the initially produced molecules may be converted using standard synthetic techniques into more desirable forms or may be fed to alternative organisms for conversion to desired products. Such molecules include, for example, glycerol, long chain alcohols, sugars, keratins, structural carbohydrates and the like. The algae themselves can be used as a carbon source in, for example, animal feed, and can themselves, upon suitable treatment such as drying, be used directly as fuel. By enhancing the level of fixed carbon, the yield of all of these useful products is increased.

It is shown herein that by co-culturing algae with heterotrophic bacteria or archaea, in particular with haloarchaea, the capacity of the algae to fix inorganic carbon, as measured on the basis of mass of carbon atoms fixed per cell, is dramatically improved by these co-cultures. (See Table 1.) The improvement may be two, three, four or even higher-fold from axenic cultures. The ultimate fate of the fixed carbon may be controlled by manipulation of metabolic pathways using standard genetic engineering techniques if desired. The resulting product may also be secreted into the medium easing the process of harvesting the biofuel.

The fixed carbon compounds can be any desired compound, provided the algae are programmed to make desired metabolites. Without further alteration, however, certain metabolites are available. The various *Dunaliella* species are currently used for production of carotenoids, glycerol, phytoene and phytofluene. Other biologicals, including lipids and amino acids, could also be harvested.

It is also shown herein that either in monoculture or in co-culture with haloarchaea, the secretion of desired products may be controlled by appropriate use of caspase inhibitors.

Hypersaline photosynthetic algae that are useful in the invention include, in addition to *Dunaliella salina*, *Dunaliella viridis*, *Dunaliella pseudosalina* and *Dunaliella parva* as well as other members of the *Chlamydomonadales* genus such as *Astrephomenaceae*, *Chlamydomonadaceae*, *Chlamydomonas*, *Chloromonas*, *Gloeomonas*, *Polytomella*, *Vitreochlamys*, and *Dunaliellaceae*.

The hypersaline photosynthetic algae are co-cultured with heterotrophic bacteria/Archaea such as haloarchaea. Suitable genera, in addition to *Halobacterium* sp., include *Haloarcula* sp., *Halferax* sp., *Haloterrigena* sp., *Halorubrum* sp., *Haladaptatus* spp., *Halalkalicoccus* spp., *Halarchaeum* spp., *Haloalcalophilium* spp., *Haloarcula* spp., *Halobaculum* spp., *Halobiforma* spp., *Halococcus* spp., *Haloferax* spp., *Halogeometricum* spp., *Halogranum* spp., *Halomarina* spp., *Halomicrobium* spp., *Halonotius* spp., *Halopiger* spp., *Haloplanus* spp., *Haloquadratum* spp., *Halorhabdus* spp., *Halorubrum* spp., *Halosarcina* spp., *Halosimplex* spp., *Halostagnicola* spp., *Haloterrigena* spp., *Halovivax* spp., *Natrialba* spp., *Natrinema* spp., *Natronobacterium* spp., *Natronococcus* spp., *Natronolimnobius* spp., *Natronomonas* spp., *Natronorubrum* spp.

In general, the conditions of co-culture include medium containing salts, nitrate, phosphate, trace metals, vitamins, but no carbon source.

The light cycle employed in the invention alternates illumination with light of (wavelengths) at intensities of 100-150-300⊠ moles photons $m^2 s^{-1}$. In general, the wavelength of light will include that absorbed by the photosynthetic mechanism of the algae. Standard illumination or sunlight may be used. Higher intensities may also be used. The cycles may have periodicities of any length, but typical periods include those mimicking a diurnal cycle, e.g., approximately 12 hours of light followed by 12 hours of darkness followed by 12 hours of light, etc. However, other cycles are also workable, and thus a light phase of 3-15 hours, 4-14 hours, 6-9 hours, may be followed by a darkness period of similar duration. The lengths of the light and darkness periods may be the same or different. Thus, 9 hours of light may be followed by 3 hours of darkness followed by 9 hours of light. The cycles may also be irregular—e.g., 9 hours of light followed by 6 hours of darkness followed by 6 hours of light followed by 10 hours of darkness, etc. While the diurnal based cycle is preferred, any light/dark/light/dark altering pattern may be employed.

The cultures are also maintained at various salt concentrations varying between 30-500 g/l, a preferred range is 100-200 g/l of sodium chloride.

In one embodiment cultures are entrained and grown in a light:dark L12 h:D12 h) photocycle at about 120 µmoles photons $m^2 s^{-1}$, 30° C. on a rotating shaker at 70 rpm in a ratio of $10^5$ algae, e.g. *D. salina*, cells to $10^8$ haloarchaea, e.g. *H. salinarum*, cells.

For either monocultures of the algae or their co-cultures with haloarchaea which are conducted with a light:dark cycle, the secretion of nutrients and fixed carbon compounds by the photosynthetic algae may be controlled by providing caspase inhibitors to be present during the dark phase of the cycle, thus delaying apoptosis and release of the nutrients until a desired time, at which time the effects of the inhibitor are neutralized.

Once the desired concentration of metabolite is reached, the caspase inhibitor is neutralized as described below, to permit apoptosis and release of the desired compounds to occur. The culture is then treated, for example, by centrifugation or filtration to recover the supernatant, and standard purification techniques are employed to obtain the desired compounds.

In an illustrative embodiment, $Zn^{+2}$ is a potent inhibitor of caspase-3 and its ability to inhibit apoptosis has been demonstrated. Addition of $Zn^{+2}$ to the culture, then, will delay apoptosis until the influence of the zinc ion is removed regardless of the light conditions. When harvest of product is desired, chelating agents may be introduced to overcome the inhibition effected by zinc ion. This permits release of fixed carbon compounds at optimum periods, rather than depending on the light:dark cycle to do so. Zinc chelators, such as diethylene triamine pentaacetic acid (DTPA) and N,N,N',N'-tetrakis(2-pyridyl methyl)ethylenediamine (TPEN) are membrane-permeable zinc chelators. Addition of these chelators to the cells permits apoptosis to occur. This effect has been demonstrated by Hashemi, M., et al. (2006) as published on the ncbi website as PubMed™ 17169355. However, if this system is used, the amount of zinc needed for inhibition of caspase inhibitors would need to be titrated as would the chelating agent since zinc ion is required by algae for carbonic anhydrase activity.

Many caspase inhibitors are known in the art. For example, Z-DEVD-FMK inhibits caspase-3 and metacaspase. Jimenez, C., et al., *X-Spot* (2009) 60:815-828. AcDEVD-CHO (*Chlorella saccharophila*), Boc D-FMK, Ac-VAD-FMK, and Ac-YEVD-CMK also inhibit caspase-3. Zuppini, A., et al., *Plant and Cell Physiol.* (2010) 51:884-895, Segovia, M., et al., *J. Physiol.* (2009) 45:1116-1126, Segovia, M., et al., *Plant Physiol.* (2003) 132:99-105. Caspases-1, 8 and 9 are also inhibited by Boc D-FMK, Ac-VAD-FMK, and Ac-YEVD-CMK. Segovia, M., et al., supra. Caspase-6 is inhibited by Boc D-FMK, Ac-VAD-FMK, and Ac-YEVD-CMK. Segovia, M., et al., supra. Metacaspase is also inhibited by zVAD-fmk, zDEVD-fmk and ac-DEVD-CHO (*T. brucei*) Deponte, M., et al., *Biochem. Biophys. ACTA* (2008) 1783:1396-1405. The Deponte article is a review of caspase inhibitors.

As to timing, cultures of the hypersaline photosynthetic algae such as *D. salina* would be grown with a constant level of caspase inhibitor. A neutralizing agent would be added when the production of the desired metabolite has peaked. When grown in co-culture with a haloarchaea, marginal apoptosis would be retained by appropriate concentration levels of the caspase inhibitor so that sufficient organic materials are secreted to supply the nutritional needs of the haloarchaea.

The following examples are intended to illustrate but not to limit the invention.

Preparation 1

*D. salina* Secretome Supports Growth of *H. salinarum*

In this preparation, *D. salina* was demonstrated to secrete all materials required for the growth of *H. salinarum* NRC-1.

Individual cultures were prepared as follows:

A *D. salina* culture in a medium that contains no fixed carbon, but which contains $NO_3$(MM1) was used to grow a culture of *D. salina* for 2 weeks. The supernatant from this culture was recovered and designated "Stationary Dun Sup."

*H. salinarum* NRC-1 was cultured in MM1, in MM1+400 mM glycerol, in MM1+NAA (a medium that contains amino acid level equivalent to that found in the natural setting of *H. salinarum*), and in Stationary Dun Sup. The salinity of all cultures was adjusted to 200 g/l.

*H. salinarum* showed no growth over 100 hours in either MM1 or MM1+400 mM glycerol. However, comparable growth to an optical density of approximately 0.25 at 600 nm was exhibited when *Halobacterium salinarum* NRC-1 was cultured either on MM1+NAA or Stationary Dun Sup. MM1, as described by Guillard, R. L., *Culture of Marine Invertebrate Animals*, Plenum Press, NY (1975) pages 29-60, contains an artificial seawater at a salinity of 200 g/l enriched with nutrients as in f/2 medium.

EXAMPLE 1

Enhancement of C-Fixation

Each of *D. salina* and *H. salinarum* were cultured separately and together in continuous light in a medium containing salts, nitrate, phosphate, trace metals, vitamins and no source of carbon. Growth and dissolved glycerol content were monitored daily or bi-daily. *H. salinarum* exhibits no growth when cultured alone in this medium, lacking a carbon source, but when co-cultured with *D. salina* growth occurs rapidly over 10-15 days, after which it declines.

Carbon fixation was measured by radioisotope labeling (incorporation of $^{14}C$).

Triplicate 50 ml flasks containing light:dark entrained pure and co-cultures of *D. salina* and *H. salinarum* were used. Carbon fixation was measured in both *D. salina* and *H. salinarum* cells.

Axenic batch cultures of *Dunaliella salina* (Culture Collection of Algae and Protozoa, UK, CCAP 19/18) were grown in artificial sea water (ASW) (Sverdrug, H., et al., *The Oceans* (Prentice-Hall, Inc., ed. 7, 1957) containing a total amount of salts reaching 200 g/L and enriched with nutrients as in f/2 media (Chantey, M. H., et al., *Culture of Marine Invertebrate Animals: Proceedings-1st Conference on Culture of Marine Invertebrate Animals Greenport* (Springer, ed. 1, 1975)) called MM1. All cultures were grown under a 13 h:11 h light:dark photocycle and with a photon flux density equal to 150 μmol photons $m^{-2}$ $s^{-1}$ (verified by a Li-Cor 191SA (Li-Cor Inc.)) at 30° C. and 100 rpm shaking. Growth rates were determined by the change in cell number and change in red fluorescence (680 nm) after 3 tandem culture transfers for acclimatization.

*Halobacterium salinarum* NRC-1 was maintained in CM (Dassarma, E. M., et al., *Archaea a Laboratory Manual: Halophiles* (Cold Spring Harbor Laboratory Press, 1995) at a salinity of 200 g/L and grown in MM1 enriched with amino acids during acclimatization to the light:dark photocycle above before co-culture experiments with *D. salina*.

C-flux was determined using radioisotope incorporation by addition of $NaH^{14}CO_3$ to an activity of 1 $\mu Ci^{14}C$ $ml^{-1}$ to these light:dark entrained pure and co-cultures of *D. salina* and *H. salinarum*. Total activity was determined with phenylethylamine (Iverson, R. L., et al., *Limnol. Oceanogr.* (1976) 21:756-758). One-ml aliquots were sampled from each culture at sequential time points and immediately fixed in 0.2% paraformaldehyde. *D. salina* and *H. salinarum* cells were collected by 2 μm and 0.22 μm filtration, respectively. $^{14}C$ uptake was halted with 250 μL 6M HCl with incubation at room temperature for 30 min and prepared for counting with the addition of Ecoscint™ (National Diagnostics). Samples were counted (disintegrations per minute, DPM) using a Tri Carb 2810 TR (Perkin Elmer) scintillation counter. The results are given in terms of mass of carbon atoms per cell.

The results are shown in Table 1.

TABLE 1

| Time | 1<br>D. salina | | 2<br>D. salina (+H. salinarum) | | 3<br>H. salinarum (+D. salina) | | 4<br>H. salinarum | |
|---|---|---|---|---|---|---|---|---|
| (hrs) | ugC/cell | std | ugC/cell | std | pgC/cell | std | pgC/cell | std |
| 0 | 0.0038691 | | 0.0038691 | | $3.869 \times 10^{-6}$ | | $2.746 \times 10^{-7}$ | |
| 8 | 1.0508678 | 0.2127935 | 0.9911266 | 0.1406961 | $1.293 \times 10^{-4}$ | $1.293 \times 10^{-5}$ | $8.696 \times 10^{-6}$ | 0 |
| 11 | 0.8556178 | 0.0548248 | 1.2938373 | 0.0419269 | $1.525 \times 10^{-4}$ | $2.166 \times 10^{-5}$ | $1.199 \times 10^{-5}$ | 0 |
| 14.5 | 0.6886038 | 0.061474 | 1.1858709 | 0.087068 | $8.595 \times 10^{-5}$ | $5.887 \times 10^{-6}$ | $1.798 \times 10^{-5}$ | 0 |
| 17.5 | 0.6934843 | 0.2364308 | 1.7239484 | 0.3635409 | $2.082 \times 10^{-5}$ | 0 | $1.556 \times 10^{-5}$ | 0 |

As shown in Table 1, column 1, when *D. salina* was cultured alone and subjected to a 12 hour:12 hour light:dark cycle, the micrograms of carbon fixed per cell increase through the light period (0-12 hours) until about hour 11, when a slight decrease occurs, presumably as a result of training in a light:dark cycle of this duration. Having reached a relatively high level of about 1 μg C/cell at the 8 hour timepoint, the content is reduced to 0.86 μg per cell at 11 hours, and by 17.5 hours the cellular content of fixed carbon is about 0.7 μg per cell.

In contrast, when co-cultured with *H. salinarum* as shown in column 2, increasing amounts are maintained through the entire light:dark cycle reaching a level of 1.72 μg per cell after 17.5 hours. This is more than twice the level obtained when the *D. salina* is cultured alone.

As shown in column 4 of the table, when *H. salinarum* is cultured alone it is unable to show the presence of any fixed carbon, as would be expected since it is not photosynthetic. As shown in column 3, while the fixed carbon is still negligible, it appears that small amounts of fixed carbon are present after 8 hours. However, these amounts are orders of magnitude less than those remaining fixed in the *D. salina* cultures.

At night, a stochastic process determines the fate of each algal cell resulting in 47% to 74% of cells undergoing apoptosis to release byproducts of photosynthetic C assimilation into the surrounding media. The byproducts are further metabolized and remineralized by archaea into a form that is readily consumed by algae. With onset of the subsequent day cycle, the algal population rapidly regenerates with up to 3 doublings with a cell division rate of 1.4 hrs. This process reiterates over the next diurnal cycle.

EXAMPLE 2

Demonstration that Apoptosis Effects Secretion of Nutrients

Axenic batch cultures of *Dunaliella salina* (Culture Collection of Algae and Protozoa, UK, CCAP 19/18) were grown in artificial sea water (ASW) (Sverdrup, H., et al., *The Oceans* (1957) (Prentice-Hall, Inc.) 7th Ed.) containing a total amount of salts reaching 200 g/L and enriched with nutrients as in f/2 media (Chantey, M. H., et al., *Culture of Marine Invertebrate Animals: Proceedings*-1st *Conference on Culture of Marine Invertebrate Animals Greenport* (1975) (Springer)) called MM1. The cultures were grown under a 13 h:12 h light:dark photocycle and with a photon flux density equal to 150 μmol photons m$^{-2}$ s$^{-1}$ (verified by a Li-Cor 191SA (Li-Cor Inc.)) at 30° C. and 100 rpm shaking. Growth rates were determined by the change in cell number and change in red fluorescence (680 nm) after 3 tandem culture transfers for acclimatization.

It was shown by merged phase contrast/fluorescence photomicrographs of a *D. salina* cell that *D. salina* stores glycerol and other byproducts of photosynthesis inside secretory vesicles that are localized to the flagellar pole. The green color of the vesicles is due to quinacrine staining of glycerol and the red fluorescence corresponds to chloroplasts. Dramatic disruption of the cell membrane and complete loss of internal glycerol occurs. Further, a shift of light acclimated cultures (100-150 μmol-photon m$^{-2}$ sec$^{-1}$) to complete darkness (0 μmol-photon m$^{-2}$ sec$^{-1}$) results in release of glycerol by *D. salina*, and intracellular glycerol, measured by flow cytometry analysis of quinacrine stained *D. salina* cells, rapidly decreases.

*Halobacterium salinarum* NRC-1 was maintained in CM (40) at a salinity of 200 g/L and grown in MM1 enriched with amino acids during acclimatization to the light:dark photocycle above before co-culture experiments with *D. salina*. The amino acid composition is as follows. All concentrations in mM unless otherwise specified. L-alanine 5.71, L-arginine HCl 1.9, L-asparagine 0.96, L-aspartate 1.88, L-glutamate 10.64, L-glutamine 5, L-glycine 1, L-histidine HCl 0.239, L-isoleucine 3.35, L-leucine 6.1, L-lysine HCl 1.04, L-methionine 0.603, L-phenylalanine 0.303, L-proline 0.4, L-serine 2.902, L-theorine 4.2, L-tryptophan 0.098, L-tyrosine 0.618, L-valine 2.135, and L-cysteine 45. The remaining components are as follows. Sodium chloride (NaCl) 3.22 M, magnesium sulfate heptahydrate (MgSO$_4$7H$_2$O) 40 mM, 3-morpholinopropane-1-sulfonic acid (MOPS) 40 mM, potassium chloride (KCl) 27 mM, sodium phosphate monobasic (NaH$_2$PO$_4$) 167 μM, folic acid 11.33 μM, thiamine HCl 14.82 μM, and biotin 2.05 μM.

It was shown that the supernatant of *D. salina* culture in artificial seawater (MM1) supported *H. salinarum* growth at a level that was comparable to its growth in MM1 supplemented with amino acids at naturally occurring concentrations.

It was also shown that *H. salinarum* induces apoptosis in *D. salina*. Intracellular glycerol within *D. salina* was stained with quinacrine and quantified with flow cytometry. Release of glycerol increased proportionally with higher cell density of *H. salinarum*, as shown in FIG. 1. On the X-axis, controls are shown for pure *D. salina* cultures grown in constant light and transferred to constant light conditions (L/L>L) and pure *D. salina* cultures grown in constant light and transferred to dark conditions (L/L>D). L/L>L is a positive control showing the maximum quantity of glycerol that can be stored by *D. salina*, and L/L>D is a negative control showing the maximum/native loss of intracellular glycerol by *D. salina*.

The open bars show the effect of *H. salinarum* co-culture density on intracellular glycerol loss. The co-cultures were grown in L/L>L conditions for 18-24 hrs. As shown, higher cell densities (measured at $OD_{600}$) of *H. salinarum* enhanced intracellular glycerol loss.

Measurements of intracellular glycerol are consistent over a period of 72 hours, the level of external glycerol increases from about 50 µmol in both pure and co-culture to about 200 µM in pure culture of *D. salina* and only to about 100 µM in co-culture with *H. salinarum*. This is consistent with the consumption of glycerol by the *H. salinarum* in co-culture.

EXAMPLE 3

Verification of Caspase 3 Involvement in Cell Death

Cell numbers for *D. salina* in pure and co-cultures with *H. salinarum* over several diurnal cycles were determined using flow cytometry. *D. salina* cells were stained with 1 uM quinacrine to highlight glycerol vesicles for 15 minutes, washed twice 200 g/L saline and analyzed for green and red fluorescence with an Influx flow cytometer (Cytopeia) using a Coherent Innova 305C argon ion laser excitation source tuned at 488 nm and 200 mW. Yellow/green fluorescent 1 µm microspheres (Polysciences, Warrington, Pa., USA) were used to calibrate gain and object detection threshold settings and as an internal fluorescence standard for normalization.

Figure 2:
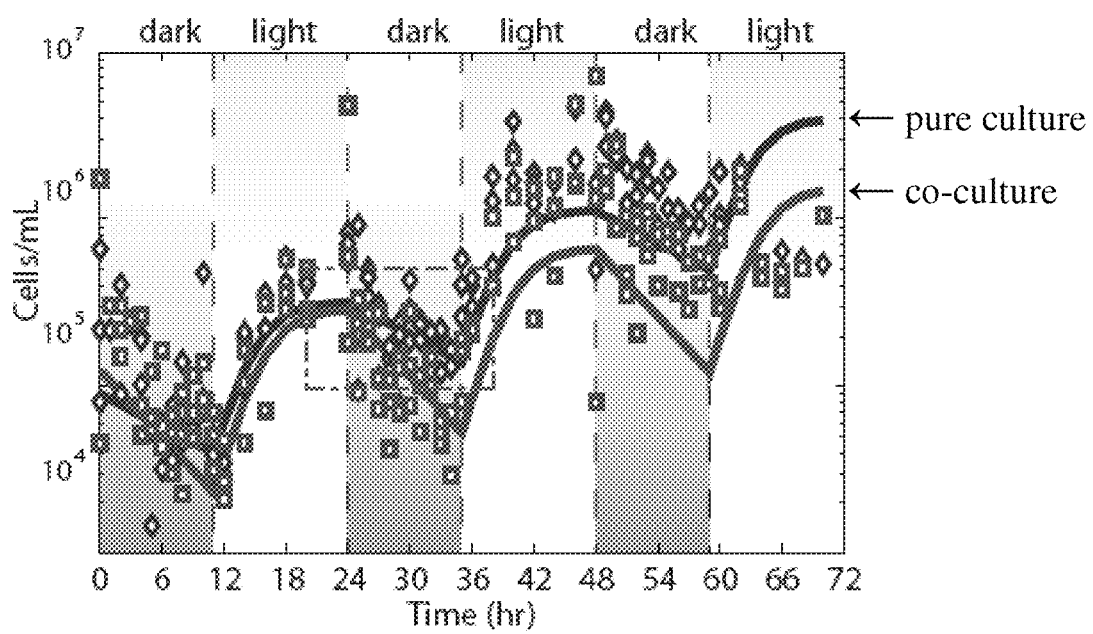
FIG. 2 shows the fluctuations in cellular density of *D. salina* in normal diurnal cycles in pure and co-culture with *H. salinarum*. It shows cell death (via apoptosis) is a natural and predominantly dark triggered occurrence in *D. salina* growth.

The results are shown in FIG. 2, providing both experimentally determined points and lines that show fitted model. FIG. 2 shows that the number of cells/ml of *D. salina* decreases during darkness and greatly increases during light to its previous level or higher and that this occurs both in pure culture and in co-culture with *H. salinarum*.

Further confirmation that secretion of glycerol during the dark cycle is correlated with cell death was the observation that those cells releasing glycerol suffered membrane damage and did not retain a nucleus which is released into the extracellular medium. This was confirmed by SYBR® green staining of DNA released from the cells and flow cytometry over a representative diurnal cycle demonstrating that indeed dead cells increase during the night. These characteristics are typical of apoptotic cells.

Figure 3:
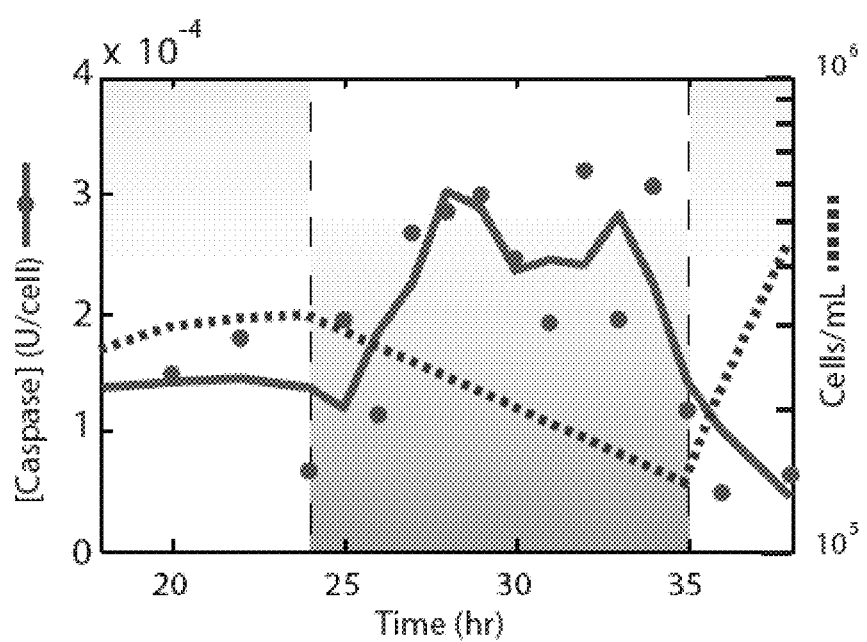
FIG. 3 shows caspase activity in *D. salina* cells relative to the diurnal cycle. Caspase is active predominantly in the dark phase, further showing that apoptosis is the mechanism for the dramatic loss of cell density during this phase.

In addition, the dark phase correlates with Caspase-3 activity. The boxed region in FIG. 2 indicates the time frame illustrated in FIG. 3 over which caspase-3 activity was assayed. Cysteine protease activity of caspase-3 was measured using a Caspase-3 Fluorometric Assay Kit (Assay Designs Catalog No. 907-014). This assay measures the conversion of a non-fluorogenic peptide Ac-DEVD-AMC substrate for caspase-3 to a fluorogenic product that emits light at 400 nm when excited at 360 nm Caspase-3 activity was calibrated with a solution of 7-amino-4-methyl coumarin at 5 µM in reaction buffer at 30° C. The dotted line shows the decrease in cell number. The solid ine shows higher levels of caspase-3 during nighttime as Savitsky-Golay smoothed (span of 5) average of two replicate measurements for each time point, verifying apoptosis.

Importantly, the intracellularly measured glycerol (~4M) content in *D. salina* combined with the number of cells observed to undergo nocturnal programmed cell death (PCD) (~3×10$^5$/mL) accounted for he majority of extracellularly measured glycerol (~70 µM), evidence that strongly supports PCD as a major mechanism for assimilated C release by *D. salina*.

EXAMPLE 4

Growth Model

Based on the observations using phase contrast time-lapse imaging of *D. salina* cells undergoing programmed cell death in response to *H. salinarum*, a model for growth in pure culture as contrasted to co-culture was derived. To facilitate imaging and localized exposure to *H. salinarum* cells, *D. salina* cells were trapped within 10 µm deep microfluidic imaging chambers. The chamber at the top of the image receives *H. salinarum* injection, while the chamber at the bottom only receives sterile growth medium. *H. salinarum* cells are injected at the 10 min timepoint. Only a subset of the chamber population are observed to undergo exocytosis/programmed cell death, consistent with total growth counts in diurnally adapted batch culture.

Growth Model Equations $$I = \begin{cases} 0, \text{Dark} \\ 1, \text{Light} \end{cases}$$

$$\dot{N} = \gamma\left(1 - \frac{N}{\kappa M}\right)NI - \delta N(1-I)$$

$$\dot{M} = \begin{cases} 0, & I = 1 \\ (N-M) - \delta M(1-I), & I = 0 \end{cases}$$

Parameters

| | Description | Units | Initial Value (Pure Culture) | Fitted Value (Pure Culture) | Initial Value (Co-Culture) | Fitted Value (Co-Culture) |
|---|---|---|---|---|---|---|
| $N_0$ | Initial cell density | Cells/mL | 9000 | — | 12500 | — |
| $M_0$ | Initial cell density saturation threshold | Cells/mL | 9000 | — | 12500 | — |
| γ | Burst growth rate | hr$^{-1}$ | 0.6262 | 0.5093 | 0.4940 | 0.5131 |
| δ | Death rate | hr$^{-1}$ | 0.0957 | 0.0740 | 0.1141 | 0.1531 |
| κ | Saturation scaling factor | — | 12.5813 | 8.073 | 12.5813 | — |

Light irradiance I was simulated as a square wave over a range of 0 (dark) and 1 (light) and a duty cycle equivalent to the nominal experimental photocycle of 11 hr:13 hr light:dark or 45.8%. The change in cellular population N, dN, was determined by two terms:

Growth:

A Verhulst/Droop algal growth model with a maximum growth rate gamma_m and a dynamic saturation constant kappa*M where kappa is an arbitrary scaling factor and M is a system memory for the cellular density at the beginning of each light phase. Subsequently the rate of change dM is zero for light phases, providing a constant saturation threshold, and resets to the current value of N during dark phases.

Death:

Exponential decay with rate delta that occurs only in the dark (1-I).

Thus, the comparative growth can be described precisely.

The invention claimed is:

1. A method to recover metabolic byproducts from a culture of hypersaline photosynthetic algae selected from the group consisting of members of Chlamydomonadales, Astrephomenaceae, Chlamydomonadaceae, Dunaliellaceae, *Chlamydomonas*, *Chloromonas*, *Dunaliella parva*, *Dunaliella pseudosalina*, *Dunaliella salina* and *Dunaliella viridis*, said method comprises:

contacting said culture with at least one caspase inhibitor in an amount effective to inhibit apoptosis, permitting said culture to generate desired amount of said metabolic byproducts, followed by contacting said culture with at least one moiety that neutralizes said inhibition of caspase, thus effecting secretion of said metabolic products, and recovering the metabolic products from the culture.

2. The method of claim 1, wherein said culture is a monoculture of said hypersaline photosynthetic algae.

3. The method of claim 1, wherein said culture is a co-culture of said algae with haloarchaea.

4. The method of claim 1, wherein the inhibitor of caspase is zinc ion and the moiety that overcomes said inhibition is a chelating agent.

5. The method of claim 1, wherein the algae are *Dunaliella salina* (*D. salina*).

6. The method of claim 2, wherein the algae are *D. salina*.

7. The method of claim 3, wherein the haloarchaea are *Halobacterium salinarum* (*H. salinarum*).

* * * * *